United States Patent [19]
Haseyama et al.

[11] Patent Number: 5,091,496
[45] Date of Patent: Feb. 25, 1992

[54] POLYISOCYANATOALKYLPHENYL-ISOCYANURATES, METHOD FOR THE PREPARATION THEREOF AND USE THEREOF

[75] Inventors: Ryuji Haseyama; Kazuyuki Kuroda; Kouzou Hayashi; Katsuyoshi Sasagawa; Taisaku Kano, all of Kanagawa; Kiyoshi Shikai, Tokyo, all of Japan

[73] Assignee: Mitsui Toatsu Chemicals, Inc., Tokyo, Japan

[21] Appl. No.: 523,467

[22] Filed: May 15, 1990

[30] Foreign Application Priority Data

| May 19, 1989 | [JP] | Japan | 1-124263 |
| Nov. 9, 1989 | [JP] | Japan | 1-290040 |
| Dec. 28, 1989 | [JP] | Japan | 1-338218 |

[51] Int. Cl.$^5$ ............................................. C08G 18/74
[52] U.S. Cl. ........................................ 528/73; 544/221; 252/182.21
[58] Field of Search ............... 544/221; 252/182.21; 528/73

[56] References Cited

U.S. PATENT DOCUMENTS 3,627,689 12/1971 Argabright .................... 560/355

*Primary Examiner*—John Kight, III
*Assistant Examiner*—Rachel Johnson
*Attorney, Agent, or Firm*—Burns, Doane, Swecker & Mathis

[57] ABSTRACT

Herein disclosed are a polyisocyanato-isocyanurate represented by the following formula (I):

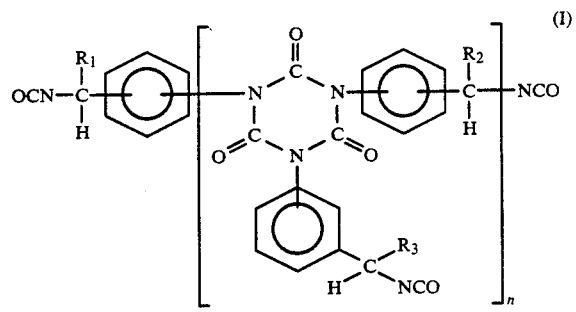

wherein n is an integer ranging 1 to 5 and $R_1$, $R_2$ and $R_3$, may be the same or different and each represents hydrogen atom or a lower alkyl group and a method for preparing it; and a resin containing an organic polyisocyanate containing not lower than 10% by weight of the polyisocyanato-isocyanurate represented by Formula (I) and a compound having at least two active hydrogen atoms as well as a resin composition for coating materials which comprises the resin.

9 Claims, 4 Drawing Sheets

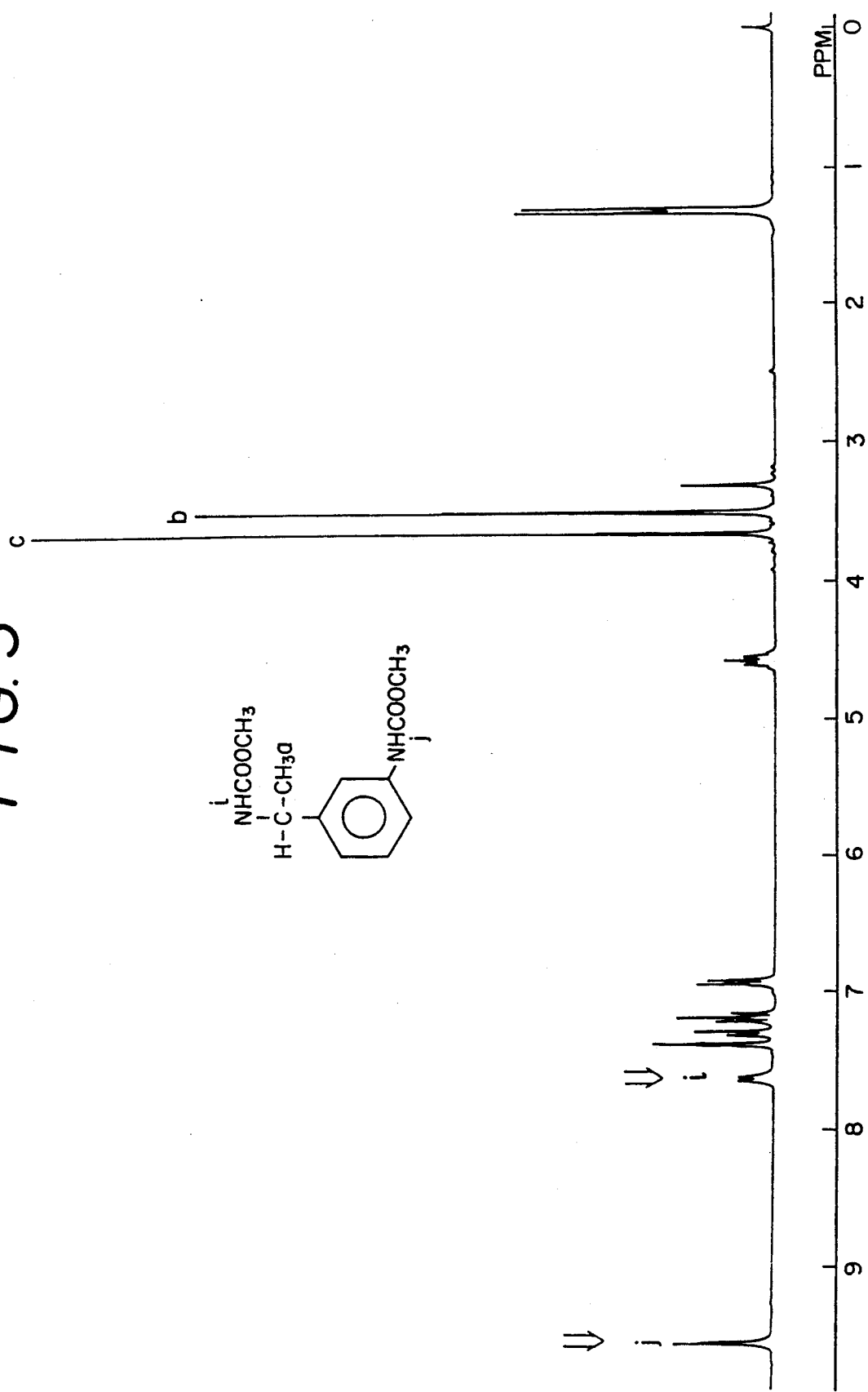

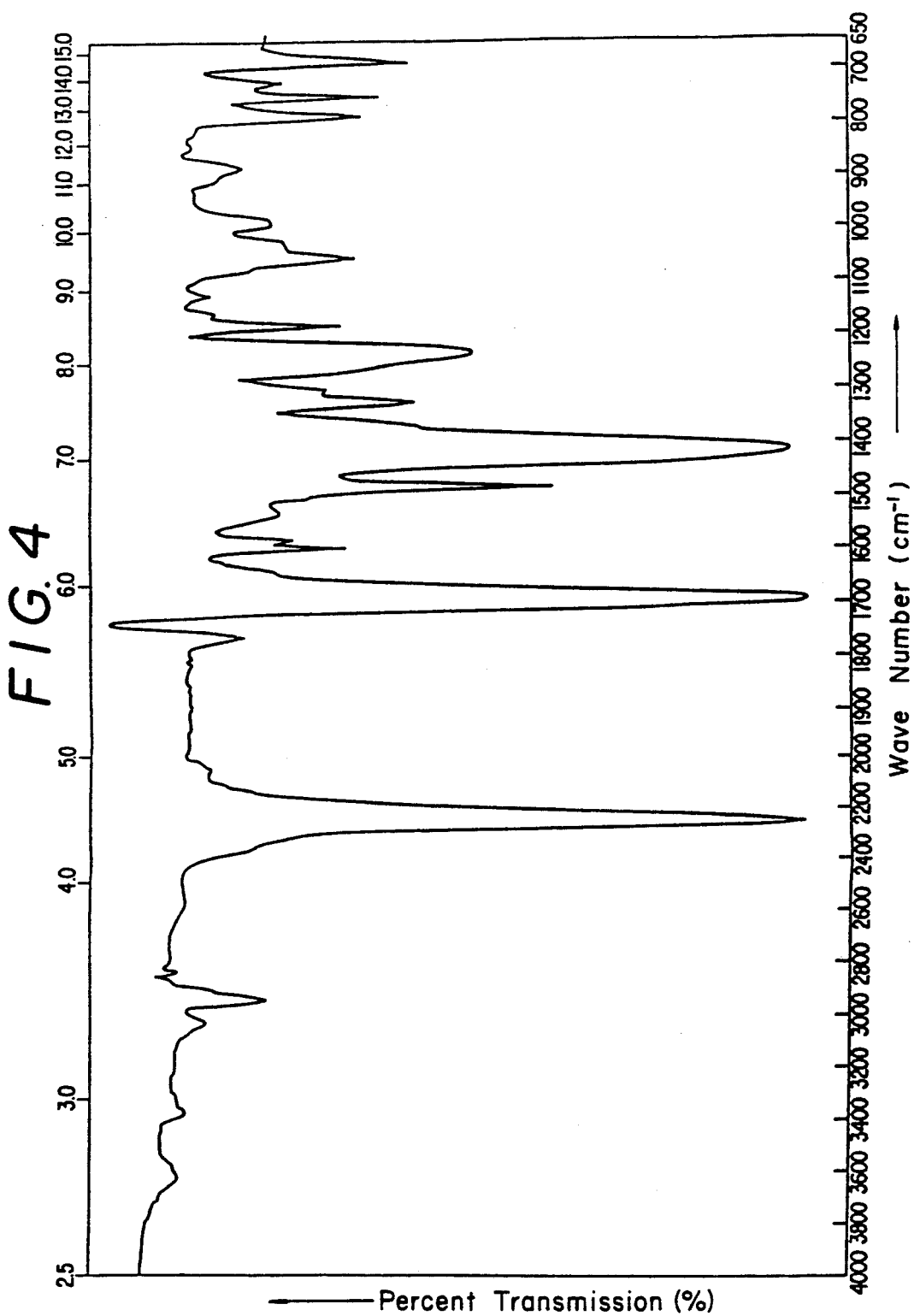

POLYISOCYANATOALKYLPHENYL-ISOCYANURATES, METHOD FOR THE PREPARATION THEREOF AND USE THEREOF

BACKGROUND OF THE INVENTION

1. Field of the Invention

The present invention relates to polyisocyanatoalkyl phenyl-isocyanurates as well as a method for the preparation of these compounds and the use thereof as isocyanate components. The polyisocyanatoalkylphenyl-isocyanurates are compounds having novel structures and can be used as expandable materials, adhesives and resins for coating materials as well as starting materials therefor.

2. Description of the Prior Art

An example of polyisocyanato-isocyanurates which have conventionally been well-known is a isocyanurate of hexamethylene diisocyanate, represented by the following formula:

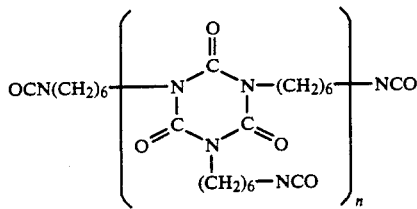

This has been widely used in various fields as a resin for two-pack urethane coating materials as well as a starting material for the resin.

Saunders & Frisch, High Polymers, Vol. XVI, Polyurethanes: Chemistry and Technology II, Technology, p. 453, proposes resins which comprise, as chief materials, alkyd resins, polyester polyols, acryl polyols or epoxy polyols and, as a hardening agent, an urethane type polyisocyanate derived from tolylene diisocyanate or an isocyanurate type polyisocyanate, as typical examples of the most general purpose resins for two-pack urethane coating materials. These resins have been used not only in coating materials for furniture and woodworking, but also in coating materials for heavy duty anticorrosion so-called tar-urethane paints. However, urethane coating materials obtained from tolylene diisocyanate show substantially low weatherability.

In order to enhance the weatherability of these resins for coating materials, there have been proposed the use of urethane type polyisocyanates derived from hexamethylene diisocyanate (HDI) (see, for instance, Japanese Patent Publication for Opposition Purpose (hereunder referred to as "J.P. KOKOKU") No. Sho 45-11146); biuret type polyisocyanates (see, for instance, U.S. Pat. No. 3,903,127); isocyanurate type polyisocyanates (see, for instance, U.S. Pat. Nos. 3,487,080, 4,324,879 and 4,412,073); urethane-modified isocyanurate type urethane isocyanates (see, for instance, Japanese Patent Un-examined Publication (hereunder referred to as "J.P. KOKAI") No. Sho 57-47321 and U.S. Pat. No. 4,582,888). Specific examples of biuret type polyisocyanates are OLESTER NP1000 (available from MITSUI TOATSU CHEMICALS, INC.) and Desmodur N-75 (available from Sumitomo Bayer Co., Ltd.); specific examples of HDI isocyanurate type polyisocyanates are Sumidur N-3500 (available from Sumitom Bayer Co., Ltd.) and CORONATE EH (available from NIPPON POLYURETHANE CO., LTD.). Organic plyisocyanates derived from an aliphatic or alicyclic compound such as isophorone diisocyanate (IPDI) or 4,4'-dicyclohexylmethane diisocyanate are also used. Specific examples of isocyanurate type polyisocyanates of IPDI include IPDI-T1890 (available from DAICEL-HUELS LTD.); and specific examples of IPDI urethane-modified polyisocyanates include IPDI-UT647 and IPDI-UT880 (available from DAICEL-HUELS LTD.). There have been used two-pack urethane coating materials which comprise these hardening agents and acryl polyols or polyester polyols as chief components.

These two-pack urethane coating materials are excellent in various properties such as weatherability, flexibility and wear resistance and secure an immovable position in, for instance, the repair of automobiles and facing of buildings and structures. However, they show insufficient drying characteristics. Therefore, they must be baked at a high temperature or must be allowed to stand for a long time period to obtain well-crosslinked tough coating material films therefrom.

As has been described above, conventional resins for two-pack urethane paints suffer from various drawbacks. For instance, tolylene diisocyanate type resins have high reactivity and hence are excellent in drying characteristics, but show substantially low weatherability, while aliphatic or alicyclic type resins are excellent in weatherability, but have unsatisfactory drying characteristics.

Moreover, it is unavoidable that, upon trifunctionalization by trimerizing diisocyanates or upon preparation of isocyanurate type polyisocyanates, pentamers or higher polymers are formed as by-products in addition to the intended trimers. In such cases, if the amount of these polymers is great, the resulting polyisocyanates have low compatibility with active hydrogen-containing compounds or solvents.

For the aforesaid reasons, it has long been desired to develop two-pack type urethane coating materials having excellent weatherability, drying characteristics and compatibility with, for instance, the foregoing active hydrogen-containing compounds or solvents.

SUMMARY OF THE INVENTION

Accordingly, a first object of the present invention is to provide a novel polyisocyanato-isocyanurate compound whose free isocyanato groups exhibit moderate reactivity and which is excellent in resistance to yellowing, weatherability and heat resistance. The polyisocyanato-isocyanurate compound has a high content of so-called trimers or a low content of pentamers and higher polymers. For this reason, excellent compatibility can be imparted to a resin which comprises an organic polyisocyanate containing the polyisocyanato-isocyanurate compound and a compound having at least two active hydrogen atoms. Thus, the polyisocyanato-isocyanurate compound whose selectivity towards trimers is high can be obtained.

A second object of the present invention is to provide a method for easily preparing polyisocyanato-isocyanurates which satisfy the foregoing requirements in a high rate of conversion and high yield.

The inventors of this invention have conducted various studies to achieve the first object of the present invention and found that this object can effectively be attained by providing a polyisocyanato-isocyanurate represented by the following general formula (I):

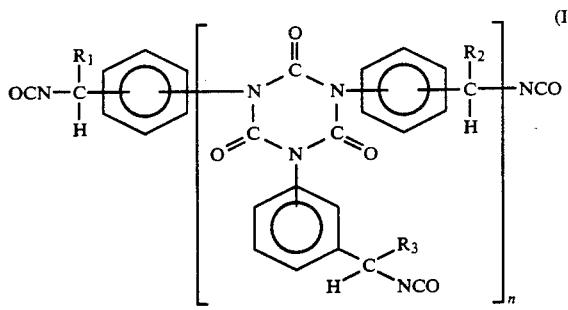

(wherein n is an integer ranging from 1 to 5 and $R_1$, $R_2$ and $R_3$ each represents a hydrogen atom or a lower alkyl group).

The polyisocyanato-isocyanurate represented by Formula (I) is very excellent in not only weatherability and yellowing resistance, but also heat resistance.

Furthermore, in the polyisocyanato-isocyanurate prepared according to the present invention, one of the two isocyanato groups present therein, linked to the secondary carbon atom which is not involved in the formation of the isocyanurate ring has moderate reactivity. Therefore, the polyisocyanato-isocyanurates show practically advantageous properties such as fast hardening speed when they are reacted, as hardening agents, with polyols or polyamines to thus obtain, for instance, resins, coating materials, films and adhesives.

The method for easily preparing the polyisocyanato-isocyanurates in a high rate of conversion and in high yield comprises polymerizing isocyanates represented by the following general formula (II):

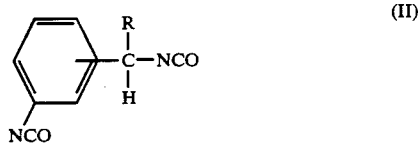

(wherein R represents a hydrogen atom or a lower alkyl group, provided that the isocyanato group attached to the phenyl group may be at either the meta- or para-position) in the presence of a proper trimerization catalyst such as a tertiary amine or a quaternary ammonium compound and optionally an epoxy compound.

According to this method, the novel isocyanurates can effectively be prepared in high selectivity, a high rate of conversion and high yield. Moreover, by-products such as higher polymers (n=6 or higher in Formula (I)) are hardly formed. Thus, the polymerization reaction may be interrupted at any desired time in the course of the reaction and the resulting reaction product may be used as such in the subsequent processes without separation and any particular purification.

A third object of the present invention is to provide a composition which comprises 10 to 100% by weight of the polyisocyanato-isocyanurate represented by Formula (I) and a resin which comprises the polyisocyanate composition and a compound having at least two active hydrogen atoms in the molecule as well as a resin composition for coating materials, which contains the foregoing resin.

BRIEF EXPLANATION OF THE DRAWINGS

FIG. 3 is an NMR chart for the methyl carbamate compound obtained by reacting methyl alcohol with m-IEBI used as a starting material in Example 1; and FIG. 4 shows an IR spectrum Chart of IEBI (rock salt plate; neat; control solution: a butyl acetate solution).

DETAILED EXPLANATION OF THE INVENTION

Figure 1:
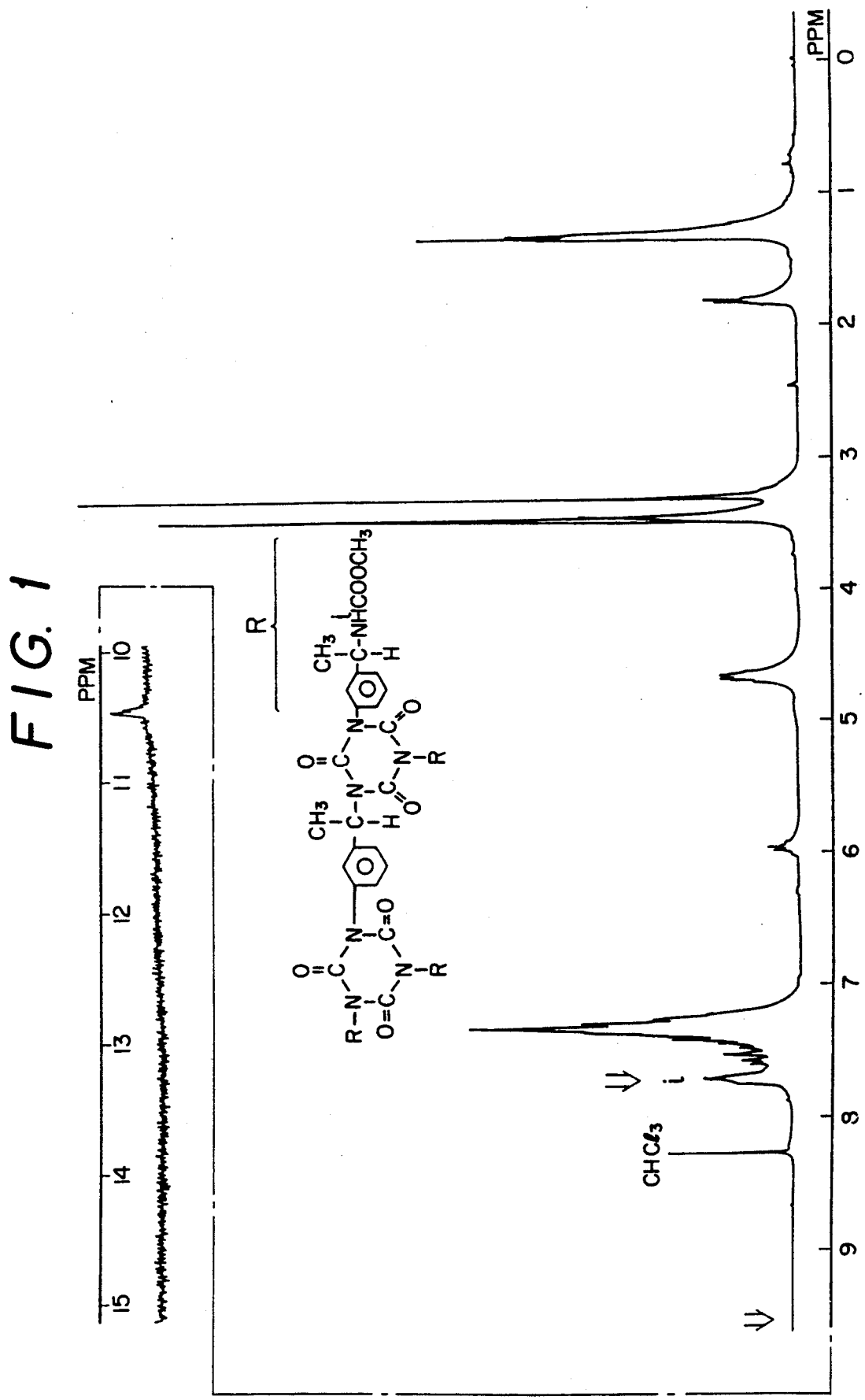
FIG. 1 is an NMR spectrum chart for the fraction (Fr.) 3 which is one of main fractions obtained by reacting N,N',N''-tris [3-(α-isocyanatoethyl)phenyl]-isocyanurate prepared in Example 1 with methyl alcohol to form a methyl carbamate compound and then subjecting the carbamate compound to fractionation by gel permeation chromatography (GPC)

The present invention will be described in more detail below.

Examples of the isocyanates represented by Formula (II) used as starting materials in the invention include α-(3-isocyanatophenyl)-ethylisocyanate, (3-isocyanatophenyl) methylisocyanate, α-(3-isocyanatophenyl)propylisocyanate, α-(3-isocyanatophenyl)-butylisocyanate, α-(3-isocyanato phenyl)pentylisocyanate, α-(4-isocyanatophenyl) ethylisocyanate, (4-isocyanatophenyl)methylisocyanate, α-(4-isocyanatophenyl)propylisocyanate, α-(4-isocyanatophenyl) butylisocyanate and α-(4-isocyanatophenyl)pentylisocyanate.

The starting materials used in the present invention are disclosed in Japanese Patent Application Serial Nos. Sho 63-298390, Hei 1-228370 and Hei 1-90676 filed by the present applicant and can be prepared according to the methods disclosed therein. More specifically, they can be prepared by a method which comprises aminating the nitro groups of nitro compounds represented by the following general formula (III) to form compounds represented by the following general formula (IV) and further aminating the carbonyl groups of the compounds (IV) to form diamine compounds represented by the following general formula (V) or a method which comprises directly converting the nitro compounds of Formula (III) into diamine compounds of Formula (V) at one step.

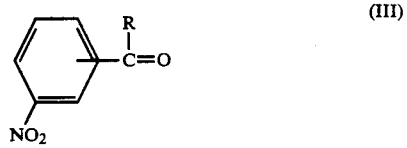

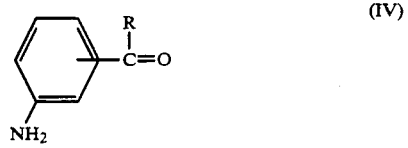

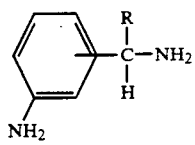

(wherein R is the same as that defined above). The latter method will hereunder be detailed below. A compound of Formula (III) is dissolved in a solvent such as methanol in an autoclave of SUS equipped with a stirring machine, a catalyst such as Raney nickel catalyst is added to the solution and the mixture is stirred. Then, ammonia is introduced into the solution while the solution is cooled to 0° to 10° C. and subsequently hydrogen gas is supplied under pressure up to about 40 atm. The temperature is raised to about 70° C. and the reaction is continued for about 60 minutes. This reaction is completed at the time when the reaction system does not absorb hydrogen gas any more. The reaction solution is then distilled in vacuo to obtain a transparent colorless distillate. This liquid is just the diamine of Formula (V).

Then, the diamine compounds of Formula (V) are phosgenated to give diisocyanate compounds of Formula (II). More specifically, o-dichlorobenzene is added to a flask equipped with a stirring machine and phosgen gas is introduced into the flask while maintaining the internal temperature at 0° to 10° C. A solution of the diamine compound of Formula (V) in o-dichlorobenzene is dropwise added to the reaction system. Phosgen gas is additionally introduced into the reaction system during the dropwise addition of the solution and the reaction is further continued for additional 2 to 3 hours. The transparent liquid in the flask changes into a pale yellowish white slurry as the reaction proceeds.

The reaction system in the form of a slurry is heated up to about 75° C. over 2 to 3 hours and thereafter hot phosgenation is performed for about two hours while introducing phosgen has. At this stage, the reaction system in the flask changes into a pale brown transparent solution.

After cooling and filtering the reaction solution, the o-dichlorobenzene and by-products are removed by distillation under reduced pressure. The resulting colorless transparent distillate is just the diisocyanate compound of Formula (II).

The polyisocyanato-isocyanurates represented by Formula (I) of the present invention are novel compounds which have just been developed recently.

Examples of the compounds of Formula (I) in which n is 1 include
N,N',N''-tris[3-( α-isocyanatoethyl)phenyl]isocyanurate,
N,N',N''-tris[3-(isocyanatomethyl)phenyl]isocyanurate,
N,N',N''-tris[3-(α-isocyanatopropyl)phenyl]isocyanurate,
N,N',N''-tris[3(α-isocyanatobutyl)phenyl]isocyanurate,
N,N',N''-tris[3-(α-isocyanatopentyl)phenyl]isocyanurate,
N,N',N''-tris[4-(α-isocyanatoethyl)phenyl]isocyanurate,
N,N',N''-tris[4-(isocyanatomethyl)phenyl]isocyanurate,
N,N',N''-tris[4-(α-isocyanatopropyl)phenyl]isocyanurate,
N,N',N''-tris[4-(α-isocyanatobutyl)phenyl]isocyanurate,
N,N',N''-tris[4-(α-isocyanatopentyl)phenyl]isocyanurate,
N,N'-bis[3-(α-isocyanatoethyl)phenyl]-N''-(3-(α-isocyanatopropyl)phenyl]isocyanurate,
N,N'-bis[3-(isocyanatomethyl)phenyl]-N''-(3-(α-isocyanatoethyl) phenyl]isocyanurate,
N,N'-bis[4-(α-isocyanatoethyl) phenyl]-N''-[4-(α-isocyanatopropyl)phenyl]isocyanurate,
N,N'-bis[4-(isocyanatomethyl)phenyl]-N''-[4-(α-isocyanatoethyl)phenyl]isocyanurate,
N,N'-bis[4-(α-isocyanatoethyl)phenyl]-N''- [3-(α-isocyanatoethyl) phenyl]isocyanurate,
N,N'-bis[4-(isocyanatomethyl)phenyl]-N''- (3-(isocyanatomethyl)phenyl]isocyanurate,
N,N'-bis[4-(α-isocyanatopropyl)phenyl]-N''-[3-(α-isocyanatopropyl) phenyl]isocyanurate,
N-[3-(α-isocyanatoethyl)phenyl]-N',N''-bis[3-(α-isocyanatopropyl)phenyl]isocyanurate,
N-[3-(isocyanatomethyl)phenyl]-N',N''-bis[3-(α-isocyanatoethyl)phenyl]isocyanurate,
N-[3-(α-isocyanatomethyl)phenyl]-N',N''-bis[4-(α-isocyanatomethyl)phenyl]isocyanurate,
N-[3-(isocyanatopropyl)phenyl]-N',N''-bis[4-(α-isocyanatopropyl) phenyl]isocyanurate,
N-[4-(isocyanatomethyl)phenyl]-N',N''-bis[4-(α-isocyanatoethyl)phenyl]isocyanurate and
N-[4-(α-isocyanatoethyl)phenyl]-N',N''-bis[4-(α-isocyanatopropyl)phenyl) isocyanurate.

In addition, examples of the compounds of Formula (I) in which n is 2, 3, 4 or 5 are oligomers of the foregoing corresponding compounds listed in connection with those of Formula (I) in which is 1.

According to the present invention, the polyisocyanato isocyanurates represented by Formula (I) can be prepared by polymerizing diisocyanate compounds represented by Formula (II) in the presence of a proper trimerization catalyst, preferably a tertiary amine or a quaternary ammonium compound and optionally an epoxide compound.

Examples of the tertiary amines used as catalysts in the foregoing method are triethylamine, tributylamine, N,N-dimethylaniline, N-ethylpiperidine, N,N'-dimethylpiperazine, Mannich bases of phenol compounds and N,N',N''-tris(dimethylaminopropyl)-hexahydro-sym-triazine.

Examples of the quaternary ammonium compounds likewise used as catalysts are hydroxides of tetraalkylammoniums such as tetramethylammonium, tetraethylammonium and tetrabutylammonium; hydroxides of hydroxyalkylammoniums such as trimethyl hydroxypropylammonium, trimethyl hydroxyethylammonium, triethyl hydroxypropylammonium and triethyl hydroxyethylammonium; and trimethyl benzylammonium hydroxide.

Examples of the epoxide compounds used in the present invention are glycidyl methyl ether, glycidyl ethyl ether, glycidyl phenyl ether and bisphenol A diglycidyl ether.

Moreover, as a reaction stopping agent, there may be used, for instance, acids such as sulfuric acid, orthophosphoric acid, polyphosphoric acid, p-toluenesulfonic acid, acetic acid, trifluoroacetic acid and benzenesulfonic acid; and acid chlorides such as benzoyl chloride and acetyl chloride.

In addition, as reaction stabilizers or storage stabilizers, organic phosphoric acid compounds and phenolic compounds can be used. Specific examples thereof are 2,6-di-tert-butyl- 4-methylphenol, triphenyl phosphite, triethyl phosphite and diisodecylpentaerythritol diphosphite.

Preferred embodiments of the method for preparing the objective compounds of Formula (I) will now be explained below.

First, a solvent for dissolving the objective compound (I) is selected and prepared. Examples of such solvents are butyl acetate, ethyl acetate, cellosolve acetate, acetone, methyl ethyl ketone, benzene, toluene and xylol.

Said isocyanate of Formula(II) is dissolved in the selected solvent at a concentration of 5 to 90% by weight, preferably 30 to 60% by weight. In this respect, the isocyanate may be used alone or in combination in a proper ratio. The preparation thus obtained is referred to as principal starting material A. It is herein noted that if the compound is used in an amount of less than 5% by weight, the objective product can be obtained, but its yield achieved is not industrially acceptable, and if the compound is used in an amount of more than 90% by weight, flowability and uniformity of the reaction are bad.

Separately, a mixture containing a catalyst or the like (hereinafter referred to as "catalyst B") and a mixture containing a reaction stopping agent (hereinafter referred to as "reaction stopping agent C") are prepared.

More specifically, the catalyst B is obtained by dissolving, in the solvent used for preparing the principal material A, a tertiary amine or a quaternary ammonium compound as the trimerization catalyst and optionally a epoxide compound as a co-catalyst. Regarding the mixing ratio, the tertiary amine is used in an amount ranging from 0.2 to 2% by weight on the basis of the weight of the solvent; the amount of the epoxide compound ranges from 0.1 to 2 moles and preferably 0.4 to 0.8 mole and the amount of the stabilizer ranges from 0.1 to 2 mole, preferably 0.5 to 1 mole, per mole of the tertiary amine. The amount of the tertiary amine ranges from 0.01 to 5% by weight, preferably 0.1 to 1% by weight of the solute (isocyanate) of the principal material A.

The stabilizer also serves to inhibit the coloring and the change of properties of the objective products during reaction and storing.

The reaction stopping agent C can be prepared by dissolving the reaction stopping agent in the solvent used for preparing the principal material A. The amount thereof dissolved in the solvent ranges from 0.5 to 5% by weight on the basis of the weight of the solvent. The reaction stopping agent is used in an amount ranging from 0.001 to 0.5% by weight, preferably 0.01 to 0.3% by weight on the basis of the total weight of the solute (isocyanate) of the principal material A.

A reaction vessel which is equipped with a stirring machine, a thermometer, a dropping funnel, a reflux condenser and a pipe for introducing an inert gas is used in the reaction by taking into consideration that this reaction system undergoes a liquid-liquid mixing reaction. The reaction vessel is preferably provided with a means for controlling the temperature of the reaction system such as those capable of heating, heat retaining or cooling the system.

A desired amount of the principal material A is introduced into the reaction vessel or a isocyanate and a solvent are introduced into the vessel and the isocyanate is dissolved in the solvent at a room temperature to prepare the principal material A and the reaction system is cooled with stirring while being blanketted with an inert gas such as nitrogen or argon gas, wherein the temperature is maintained at $-10°$ C. to a room temperature, preferably 0° to 10° C.

The catalyst B is dropwise added to the solution over 10 to 30 min., the temperature is raised to T °C. and the reaction is continued for 0.5 to 15 hours. In this case, the temperature T ranges from 0° to 80° C., preferably 5° to 30° C. If the temperature is lower than 0° C., the objective polyisocyanato-isocyanurate can be obtained, but the yield and/or the reaction rate are not industrially acceptable, while if it is higher than 80° C., the polyisocyanatoesocyanurate can of course be obtained. However, the yield of the product of Formula (I) wherein n is 1 decreases, while not only that for each product of Formula (I) in which n is 2, 3, 4 or 5 is increased, but also the product having n of 6 or higher is increased.

Lap samples of the reaction are collected and the amount of unreacted isocyanate is determined in terms of gas chromatography. A reaction terminator C is dropwise added to the reaction system at the time when the amount of the unreacted isocyanate reaches a predetermined level. Thereafter, the temperature of the reaction system is brought back to room temperature with stirring.

Figure 2:
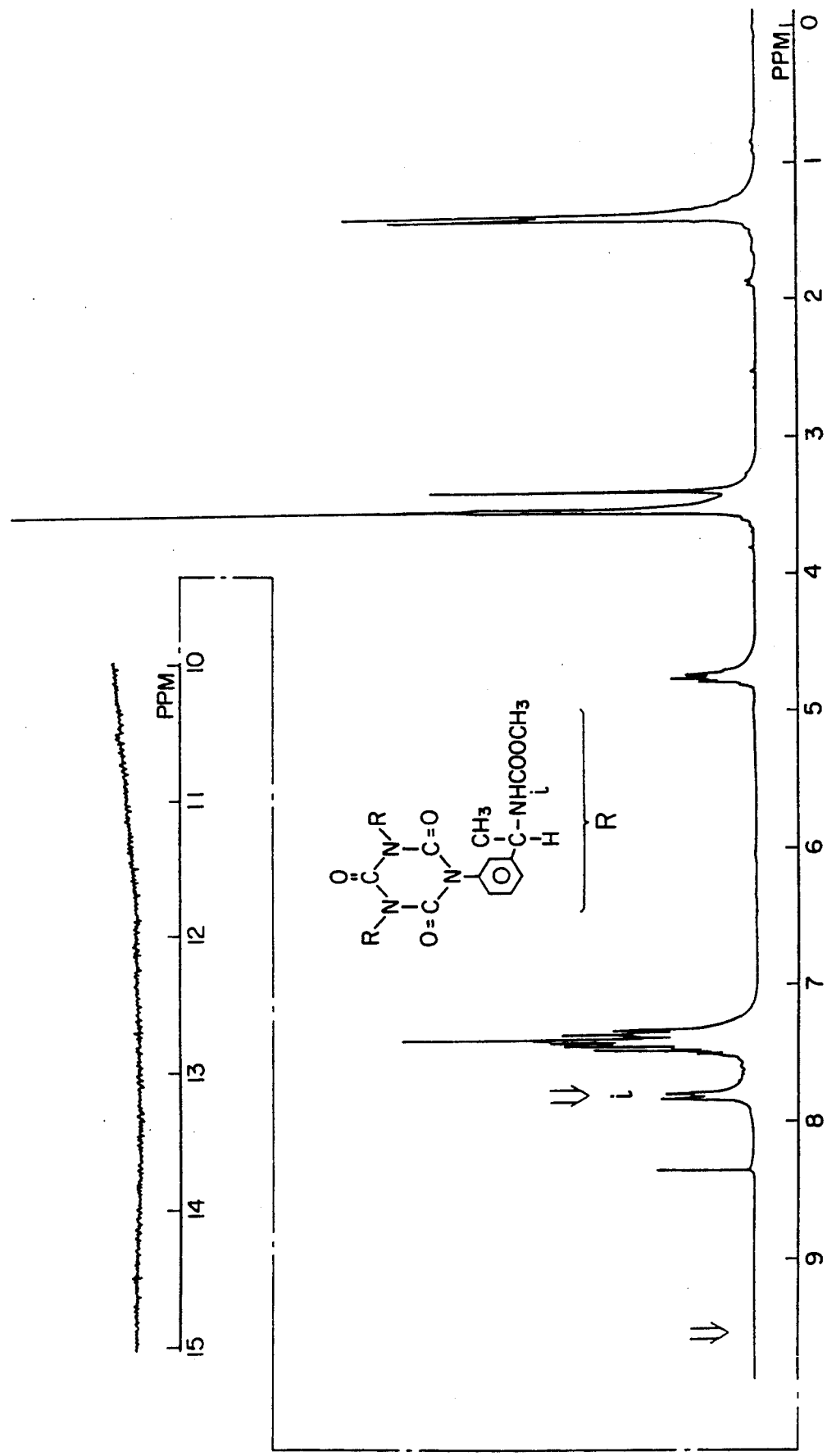
FIG. 2 is an NMR chart for the Fr. 4 which is another main fraction obtained through the aforesaid GPC fractionation in Example 1.

The reaction product is reacted with methyl alcohol to form a methyl carbamate compound and the compound is subjected to GPC to fractionate it into fractions (Fr.). Each fraction is analyzed by NMR spectroscopic measurement and FD-MS measurement. The results thus obtained are shown in FIGS. 1 to 3.

As a result, it is found that the main components thereof (i.e., Fr. 3 and Fr. 4) among the resulting fractions do not have structures of the following types B and C, but have a structure of the following type A and that in the structure A, n is 2 for Fr. 3 and 1 for Fr. 4.

Structure of Type A:

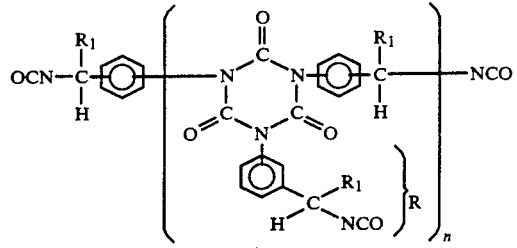

Structure of Type B:

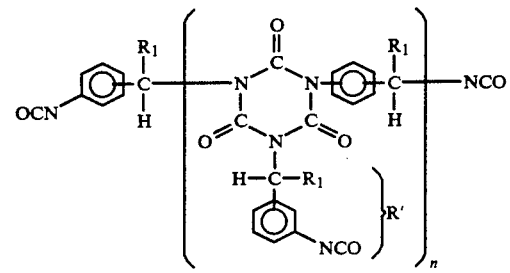

Structure of Type C:

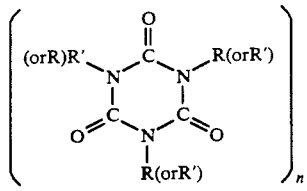

The chemical shift of the —NH— group in the urethane bond is detected at 7.7 ppm for Fr. 3 and 7.8 ppm for Fr. 4. This can be described to the —NH—* group of the type A on the basis of the results of $^1$H-NMR spectroscopic measurement on the methyl carbamate compound obtained by reacting the starting isocyanate with methyl alcohol. At the same time, the chemical shift of the —NH—** group of the type B structure should be found around 9.6 ppm, but no signal is detected at the corresponding position.

*: —NH— group of type A:

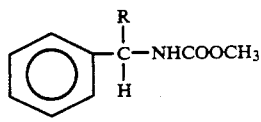

**: —NH— group of type B:

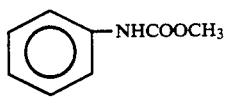

This fact clearly indicates that the both compounds have the structure of type A. In other words, it is analytically confirmed that the reactivity of the two isocyanato groups present in the structure differ from one another and that upon trimerization, the isocyanato group having high reactivity and directly bonded to the benzene ring is involved in the formation of the isocyanurate ring while the other isocyanato group bonded to the secondary carbon atom is in the free state.

Namely, the method of the present invention makes it possible to selectively prepare the novel compounds of Formula (I) in which, upon trimerization, one of the two isocyanato groups having high reactivity, directly bonded to the benzene ring is involved in the formation of the isocyanurate ring while the other isocyanato group bonded to the secondary carbon atom is in the free state since the reactivity of these two isocyanato groups present in the structure differ from one another. Moreover, according to the method of this invention, trimers (n=1) are formed at a relatively high selectivity and pentamers (n=2) and heptamers (n=3) are formed, but polymers (n=6 or higher) are scarcely formed. Thus the method of this invention makes it possible to prepare a polyisocyanato-isocyanurate mixture comprising the trimer (n=1) in an amount of not lower than 40% by weight in good reproducibility.

In addition, if the amount of the unreacted isocyanate is reduced to not higher than 1% by weight, the reaction product together with the solvents can be employed as starting materials for various uses, by making the best use of the high selectivity and yield of the method.

In addition, the inventors of this invention have conducted various studies to solve the problems associated with the conventional two-pack urethane coating materials, have found that the resins for two-pack urethane coating materials which comprise the polyisocyanato-isocyanurate represented by Formula (I) and a compound having at least two active hydrogen are excellent in drying properties and weatherability and thus have completed the present invention.

Consequently, the present invention relates to a resin composition for two-pack urethane coating materials which comprises an organic polyisocyanate containing 10 to 100% by weight of the polyisocyanato-isocyanurate of Formula (I) and a compound having at least two active hydrogen atoms in the molecule.

The organic polyisocyanate containing 10 to 100% by weight of the polyisocyanato-isocyanurate of Formula (I) which is used in the resin composition for two-pack urethane coating materials according to the present invention herein means a polyisocyanate obtained through the foregoing trimerization reaction, or a mixture thereof with a modified product of an aliphatic or alicyclic compound such as hexamethylene diisocyanate, isophorone diisocyanate or 4,4'-dicyclohexylmethane diisocyanate obtained through the reaction with urethane and/or biuret.

In this mixture, if the amount of the polyisocyanato-esocyanurate represented by Formula (I) is less than 10% by weight, it is difficult to obtain resins for two-pack urethane coating materials having good drying properties.

Examples of the compounds having at least two active hydrogen atoms used in the invention are glycols, alkane polyols, polyether polyols, polyester polyol resins, acryl polyol resins, epoxy resins or monomers or polymers of aromatic or heterocyclic polyhydric alcohols.

Specific examples thereof include glycols such as ethylene glycol, propylene glycol, beta,beta'-dihydroxydiethyl ether (diethylene glycol), dipropylene glycol, 1,4-butylene glycol, 1,3-butylene glycol, 1,6-hexamethylene glycol, neopentyl glycol, polyethylene glycol, polypropylene glycol, polypropylene-poly-ethylene glycol and polybutylene glycol; alkane polyols such as glycerin, trimethylolpropane, hexanetriol, pentaerythritol, xylitol and sorbitol; polyether polyols obtained by adding an alkylene oxide or mixture thereof (for instance, ethylene oxide, propylene oxide and 1,2-butylene oxide) to a polyhydric alcohol or mixture thereof such as glycerin or propylene glycol; polyether polyols such as those obtained by reacting alkylene oxide with polyfunctional compounds such as ethylenediamine or ethanolamine; polyester polyol resins such as those obtained by condensing a polyhydric alcohol or mixture thereof selected from the group consisting of, for instance, ethylene glycol, propylene glycol, diethylene glycol, dipropylene glycol, 1,4-butylene glycol, 1,3-butylene glycol, 1,6-hexamethylene glycol, neopentyl glycol, glycerin and trimethylolpropane with a dibasic acid or mixture thereof selected from the group consisting of succinic acid, adipic acid, sebacic acid, dimer acids, maleic anhydride, phthalic anhydride, isophthalic acid and terephthalic acid; acryl polyols obtained by, for instance, copolymerizing polymerizable monomer having at least one active hydrogen in the molecule with copolymerizable other monomers; acryl polyol resins such as those obtained by polymerizing acryl esters having active hydrogen atoms (for instance, 2-hydroxyethyl acrylate, 2-hydroxypropyl acrylate and 2-hydroxybutyl acrylate), methacrylates having active hydroxypropyl methacrylate and 2-hydroxybutyl methacrylate), acrylic acid monoester or methacrylic acid monoester of glycerin, acrylic acid monoester or methacrylic acid monoester of trimethylolpropane or mixture thereof; with acrylic acid esters (for instance, methyl acrylate, ethyl acrylate, isopropyl acrylate, n-butyl acrylate and 2-ethylhexyl acrylate), methacrylic acid esters (for instance, methyl methacrylate, ethyl methacrylate, isopropyl methacrylate, n-butyl methacrylate, isobutyl methacrylate, n-hexyl methacrylate and lauryl meth-acrylate) or mixture thereof; in the presence of or absence of unsaturated carboxylic acids (for instance, acrylic acid, methacrylic acid, maleic acid and itaconic acid), unsaturated amides (for instance, acrylamide, N-methylol acrylamide and diacetone acrylamide), or other polymerizable monomers (for instance, glycidyl methacrylic acid, styrene, vinyl toluene, vinyl acetate and acrylonitrile) or mixture thereof; and epoxy resins such as those novolak type, β-methylepichlo type, cyclic oxirane type, glycidyl ether type, glycidyl ester type, glycol ether type, epoxylated aliphatic unsaturated compound type, epoxylated aliphatic ester type, polycarboxylic acid ester type, aminoglycidyl type, halogenated type and resorcin type ones. Monosaccharides such as fruit sugar, grape sugar, cane sugar, milk sugar, 2-methyl glycoside and derivatives thereof; and aromatic or heterocyclic polyhydric alcohols such as trimethylolbenzene and tris(2-hydroxyethyl)esocyanurate are also included in addition to the foregoing compounds. These compounds may be used alone or in combination or further in combination with at least one member selected from the group consisting of other compounds having at least two active hydrogen atoms such as primary or secondary amino group-containing compounds (for instance, ethylenediamine, triethylenediamine, hexamethylene-diamine, m-xylylenediamine, diaminodiphenylmethane, isophorone-diamine, diethylene triamine, polyamines such as those obtained by adding various alkylene polyamines to alkylene oxides and N,N'-dimethylethylenediamine), substituted urea compounds (for instance, N,N'-dimethyl urea and N-methyl-N'-cyclohexyl urea), mercapto group-containing compounds (for instance, 1,2-ethane-dithiol, 1,6-hexanedithiol, polyether polythiol and polyester polythiol), carboxyl group-containing compounds (for instance, succinic acid, adipic acid, sebacic acid, terephthalic acid and polybutadiene having carboxyl termini), or compounds having different groups containing active hydrogen atoms in the molecule (for instance, monoethanolamine, thioethanolamine, lactic acid and β-alanine).

Although various compounds having active hydrogen atoms have been exemplified above specifically, the present invention is not restricted to these compounds specifically listed above and any compounds having active hydrogen atoms may be employed so far as they can react with polyisocyanates used in making resin compositions for two-pack urethane coating materials according to the present invention and any combination of these compounds may be employed.

When the both components of the resin compositions for two-pack urethane coating materials according to the present invention are mixed together, appropriate solvents may optionally be used. Such solvent is properly selected, depending on the purposes and applications, from the group consisting of, for instance, hydrocarbons (for instance, benzene, toluene, xylene, cyclohexane, mineral spirits and naphtha), ketones (for instance, acetone, methyl ethyl ketone methyl isobutyl ketone) and esters (for instance, ethyl acetate, n-butyl acetate, cellosolve acetate and isobutyl acetate). These solvents may be used alone or in combination.

The resin compositions of the present invention may further comprise other additives commonly employed in this field, depending on the purposes and applications, such as catalysts, pigments, leveling agents, antioxidants, plasticizers and surfactants.

In general, polyurethane coating materials have adhesion to materials to be coated therewith, hardness and flexibility which are well-balanced with each other and are excellent in resistance to cracking, water resistance, resistance to chemicals, luster and appearance. On the other hand, the polyurethane coating obtained by applying the composition of the present invention as a coating material shows excellent weatherability and photostability in addition to the foregoing properties. Further, the coated film provides the following excellent characteristics compared with commercially available coating materials. First, the isocyanurate type polyisocyanate used in the composition of the invention has high initial curing and drying properties compared with aliphatic polyisocyanates such as organic polyisocyanates derived from hexamethylene diisocyanate and is excellent in compatibility. Therefore, the coated film has very excellent appearance and coated film performance thereof are comparable to or higher than those for coated films derived from commercially available coating materials. Thus, they are favorable for use in applications such as coating of vehicles in which workability, appearance and coated film performance are regarded as of major importance.

The present invention will hereinafter be explained in more detail with reference to the following non-limitative Examples and Reference Examples.

REFERENCE EXAMPLE 1

Preparation of α-(3-aminophenyl) ethylamine 33.0 g (0.2 mole) of m-nitroacetophenone, 200 ml of methanol and 4.6 g (expressed in the reduced amount of nickel) of Raney nickel were introduced into a 500 ml inner volume autoclave of SUS 316L equipped with a stirring machine, the internal atmosphere was replaced with nitrogen gas and the contents of the autoclave was stirred for a while.

Then about 40 g of ammonia was introduced into the autoclave while cooling the reaction system with ice-water. Subsequently, hydrogen gas was supplied thereto under pressure up to a pressure of 40 kg/cm$^2$ G and the temperature of the reaction system was raised to 70° C. The reaction was continued at that temperature for 55 minutes and the reaction was stopped at a time when the amount of hydrogen gas absorbed reached 16.7 Nl, since at this stage absorption of hydrogen did not proceed any more. The reaction system was allowed to cool down to room temperature, withdrawn from the autoclave, filtered and the filtrate was distilled at a pressure of 5 to 6 mmHg to thus give 23.9 g (0.175 mole) of a distillate having a boiling point of 120° to 122° C. (yield=88.0%).

The resulting liquid was colorless and transparent and was identified to be α-(3-aminophenyl)ethylamine (hereunder referred to as "APEA) on the basis of the results of elemental analysis, GC-MS spectroscopic measurement, H-NMR spectroscopic measurement and IR spectroscopic measurement. The results of these measurements are shown below.

The product was analyzed by gas chromatography and it was found that the purity thereof was 99.3%.

(1) Elemental Analysis (for $C_8H_{12}N_2$): Calculated (%): C 70.48; H 8.81; N 20.56; Found (%): 70.45; 8.91; 20.38.

(2) GC-MS Spectra: EI-MS spectrum:$(M^+)=136$ (Note: molecular weight of APEA $(C_8H_{12}N_2)=136.2$).

(3) IR Spectra (rock salt plate; neat) $cm^{-1}$: 3400, 3340, 3190, 2940, 1600, 1485, 1455, 1360, 1310, 1160.

REFERENCE EXAMPLE 2:

Preparation of α-(3-isocyanatophenyl) ethylisocyanate (hereunder referred to as "m-IEBI")

In this Reference Example, α-(3-aminophenyl)ethylamine as a starting material was phosgenated according to a cold-hot-two-stage method. To a 2 l reaction flask equipped with a stirring machine, a thermometer, a tube for introducing phosgen gas, a condenser and a dropping funnel, 800 g of o-dichlorobenzene was added, the flask was dipped in an ice-water bath with stirring to maintain the internal temperature to about 2° C. and phosgen gas was introduced into the flask for one hour at a rate of 75 g/h. Then a solution of 40 g (0.294 mole) of the foregoing diamine in 307 g of o-dichlorobenzene was dropwise added to the flask over one hour. During the dropwise addition of the diamine, cold phosgenation was performed at a temperature ranging from 2 to 7° C. with the introduction of phosgen gas at a rate of 75 g/h and, after the dropwise addition, phosgen gas was additionally introduced into the flask at a temperature ranging from 7° to 16° C. for 30 minutes at a rate of 50 g/h. After the dropwise addition, the reaction system changed into a pale yellowish white slurry. Then the temperature of the contents of the flask was raised up to 74° C. over 2.5 hours with the introduction of phosgen gas at a rate of 50 g/h. After raising the temperature, hot phosgenation was performed at a temperature ranging from 74° to 100° C. for 2 hours while continuing the introduction of phosgen gas. The contents of the flask charged into a pale brown transparent solution during the hot phosgenation. Consequently, 210 g (2.12 mole) of phosgen gas in total was introduced during the cold-hot two-stage phosgenation. This corresponds to about 3.6 times the stoichiometric amount thereof. After the completion of the hot phosgenation, nitrogen gas was introduced into the flask at 90° C. for 2 hours to perform degassing. After cooling and filtering the reaction system, the resultant filtrate was distilled under reduced pressure to remove the solvent, i.e., o-dichlrobenzene to thus give about 55 g of a brown reaction solution The reaction solution was further distilled under reduced pressure to remove a small amount of a by-product: α-(3-isocyanatophenyl)ethyl chloride to thus give about 44.7 g (0.238 mole) of a distillate (a colorless transparent liquid; NCO content=44.61%) having a boiling point of 136° C./10 mmHg. The result of the elemental analysis of this distillate is as follows:

Elemental Analysis (for $C_{10}H_8N_2O_2$): Calculated (%): C 63.76; H 4.25; N 14.88; Found (%): 63.86; 4.22; 14.91.

In addition, GC-MS Spectroscopic measurement provides $(M^+)$ of 188 which is well consistent with the molecular weight (188.2) of the compound represented by Formula (II). Moreover, the distillate was identified to be α-(3-isocyanatophenyl)ethylisocyanate in terms of the results of IR and $^1H$-NMR spectroscopic measurements.

EXAMPLE 1

Preparation of N,N',N''-tris[3-(α-isocyanatoethyl)phenyl]isocyanurate (1) Preparation of a Mixture Comprising Catalysts or the Like (Catalyst B):

The catalyst B was prepared by dissolving the following catalyst and other components in butyl acetate as a solvent.

Trimerization catalyst N,N',N''-tris(dimethylaminopropyl) hexahydro-sym-triazine (U-CAT SA-410; available from SAN-APRO Co., Ltd.): 0.1 g $(2.92 \times 10^{-4}$ mole)

Cocatalyst: bisphenol A diglycidyl ether: 0.1 g $(1.80 \times 10^{-4}$ mole)

Stabilizer: diisodecyl pentaerythritol diphosphite (HI-M-O; available from SANKOU CHEMICAL CO. LTD): 0.12 g $(2.36 \times 10^{-4}$ mole)

Solvent: butyl acetate: 7.5 g $(6.45 \times 10^{31\ 2}$ mole)

(2) Preparation of Terminator C

The terminator was prepared by dissolving 0.5 g (expressed in the reduced amount of $P_2O_5$; $3.00 \times 10^{-3}$ mole) in 25 g of butyl acetate.

(3) Reaction

To a 30 ml four-necked flask, there were added 10.05 g (0.053 mole) of α-(3-isocyanatophenyl)ethylisocyanate (hereunder referred to as "m-IEBI") synthesized by phosgenation of α-(3-aminophenyl)ethylamine (see Reference Example 2) and 8.51 g (0.073 mole) of butyl acetate as a solvent, to dissolve the isocyanate and the solution was cooled to 5° C. with stirring while the content of the flask was blanketed with nitrogen gas. The catalyst B (1.20 g; $4.48 \times 10^{-5}$ mole) prepared above was added to the solution with stirring and as the stirring was continued and the trimerization reaction proceeded, the temperature of the solution rose up to 22° C. Thereafter, the flask was externally cooled or warmed to control the temperature of the solution to 22° C.

Lap samples were collected at predetermined intervals and the amount of unreacted free m-IEBI in each sample was determined by gas chromatography. The amount thereof reached a predetermined level (not higher than 1% by weight) about 10 hours after the addition of the catalyst B. Thus, the terminator C (0.37 g; $4.35 \times 10^{-5}$ mole) prepared above was added to the reaction system, stirring was further continued for additional one hour, then the stirring was stopped and the contents of the flask were withdrawn. The weight of the contents was determined and found to be 18.8 g. Since the initial charge weight was 20.1 g (solid content=10.1 g), the loss of weight was equal to 1.3 g.

The results of analysis of this product was as follows:
Solid content (nonvolatile content): 50.0% by weight
NCO content: 9.37% by weight
Free m-IEBI: 0.11% by weight If the weight loss due to the withdrawal of the lap samples and the evaporation of the solvent is taken into consideration, 50.0/50.2 =0.996 which means that the yield is not lower than 99%.

Then a part of the resulting polyisocyanato-isocyanurate was reacted with methyl alcohol to form a methyl carbamate compound and the compound was fractionated by GPC to give fractions. Each fraction was analyzed by NMR and FD-MS measurements. The results thus obtained are shown in FIGS. 1 to 3.

The masses of the Frs. 3 and 4 as determined by FD-MS measurement were 1068 and 660 respectively. These masses are well consistent with the methyl carbamate compounds of Formula (I) in which n is 2 and 1 respectively.

Moreover, the chemical shift of the —NH— group in the urethane bond was detected at 7.7 ppm for the Fr. 3 and 7.8 ppm for the Fr. 4 as seen from the NMR chart illustrating chemical shifts of these compounds. This can be ascribed to the —NH—* group of the type A structure in the light of the $^1$H-NMR spectra of the methyl carbamate compound of m-IEBI. At the same time, the chemical shift of the —NH—** group of the type B structure should be found around 9.6 ppm, but no signal was detected at the corresponding position. This fact clearly indicates that the both compounds have the structure of type A.

In addition, it was found that the amount of each oligomer was as follows on the basis of the results of GPC analysis of the methyl carbamate compound:
n=1 (trimer): 72.9%
n=2 (pentamer): 20.1%
n=3 (heptamer): 5.6%
n=4 and 5: 1.4%

As seen from the results of the GPC analysis, polyisocyanato isocyanurate containing not lower than 40% by weight of trimers (n=1) could be obtained without accompanying the formation of higher polymers (n=6 or higher).

FIG. 4 shows a chart of IR spectroscopy (rock salt plate; neat; control solution: butyl acetate solution).

In FIG. 4, the absorption bands ranging from 1400 to 1420 cm$^{-1}$ and from 1690 to 1700 cm$^{-1}$ are ascribed to the isocyanurate ring and that ranging from 2220 to 2230 cm$^{-1}$ corresponds to the isocyanato group.

The resulting N,N',N"-tris (3-($\alpha$-isocyanatoethyl) phenyl) isocyanurate was subjected to thermal analysis and it was confirmed that it exhibited very excellent heat resistance. Moreover, the glass transition point of the resin obtained by polymerization in which the compound was used as a hardening agent was increased and when the weatherability thereof was examined, it was found that it showed almost no yellowing, i.e., high resistance to yellowing. Thus, it is confirmed that the foregoing reaction product is a compound having useful properties.

EXAMPLE 2

Preparation of
N,N',N"-tris[3-($\alpha$-isocyanatoethyl)phenyl]isocyanurate (a catalyst different from that used in Example 1 was used)

(1) Preparation of a Mixture Comprising Catalysts or the Like (Catalyst B)

The catalyst B was prepared by dissolving the following catalyst and other components in butyl acetate as a solvent.

Trimerization catalyst: 40% methanol solution of trimethylbenzyl-ammonium hydroxide: 1.0 g (2.39×10$^{-3}$ mole)
Cocatalyst: bisphenol A diglycidyl ether: 0.1 g (1.80×10$^{-4}$ mole)
Stabilizer: triphenyl phosphite: 0.1 g (3.23×10$^{-4}$ mole)
Solvent: butyl acetate: 8.8 g (7.57×10$^{-2}$ mole)

(2) Preparation of Terminator C

The terminator C was prepared by dissolving 0.5 g (expressed in the reduced amount of P$_2$O$_5$; 3.00×10$^{-3}$ mole) in 12.5 g of butyl acetate.

(3) Reaction

To a flask similar to that used in Example 1, there were added 10.00 g (0.053 mole) of m-IEBI and 9.10 g (0.078 mole) of butyl acetate as a solvent, to dissolve the m-IEBI and the solution was cooled to 5° C. with stirring while the content of the flask was blanketed with nitrogen gas. The catalyst B (1.00 g; 2.39×10$^{-4}$ mole) prepared above was added to the solution with stirring and when the stirring (600 rpm) was continued, the temperature of the solution initially rose up to 20° C. due to the heat of reaction Thereafter, the flask was externally cooled or warmed to control the temperature of the solution to 28° C.

Lap samples were collected at predetermined intervals and the amount of unreacted free m-IEBI in each sample was determined by gas chromatography. The amount thereof reached a predetermined level (not higher than 1% by weight) about 12 hours after the addition of the catalyst B. Thus, the terminator C (prepared in the same manner as in Example 1; 1.00 g; 2.31×10$^{-4}$ mole) was added to the reaction system, stirring was further continued for additional one hour at a temperature of 28° C., then the stirring was stopped and the contents of the flask were withdrawn.

The weight of the contents was determined and found to be 18.8 g.

The results of analysis of this product was as follows:
Solid content (nonvolatile content): 48.5% by weight
NCO content: 9.18% by weight
Free m-IEBI: 0.52% by weight
The yield of this reaction was not lower than 99.0%.

Then a part of the resulting polyisocyanato-isocyanurate was reacted with methyl alcohol to form a methyl carbamate compound and the compound was fractionated by GPC to give fractions. Each fraction was analyzed in the same manner as in Example 1 and it was found that the amount of each oligomer was as follows:
n=1 (trimer): 73.9%
n=2 (pentamer): 20.7%
n=3 to 5: 5.9%

The N,N',N"-tris[3-($\alpha$-isocyanatoethyl)phenyl]isocyanurate obtained in this Example was likewise subjected to thermal analysis and it was also confirmed that it exhibited very excellent heat resistance. Moreover, the glass transition point of the resin obtained by polymerization in which the compound was used as a hardening agent was increased and when the weatherability thereof was examined, it was found that it showed almost no yellowing, i.e., high resistance to yellowing. Thus, it is confirmed that the foregoing reaction product is a compound having useful properties.

EXAMPLE 3

Preparation of
N,N',N"-tris[4-($\alpha$-isocyanatoethyl)phenyl]isocyanurate

As in Example 1, there were added, to a 30 ml four-necked flask, 10.00 g (0.053 mole) of $\alpha$-(4-isocyanatophenyl) ethylisocyanate (hereunder referred to as "p-IEBI") obtained by phosgenation of $\alpha$-(4-aminophenyl)ethylamine and 9.00 g (0.077 mole) of butyl acetate as a solvent to dissolve the p-IEBI and the solution was cooled to 5° C. with stirring while the content of the flask was blanketed with nitrogen gas.

The catalyst B (1.20 g; 4.50×10⁻⁵ mole) prepared in Example 1 was added to the solution with stirring and as the stirring was continued and the trimerization reaction proceeded, the temperature of the solution rose up to 34° C. Thereafter, the flask was externally cooled or warmed to control the temperature of the solution to 25° C.

Lap samples were collected at predetermined intervals and the amount of unreacted free p-IEBI in each sample was determined by gas chromatography. The amount thereof reached a predetermined level (not higher than 1% by weight) about 9 hours after the addition of the catalyst B. Thus, the terminator C (prepared in the same manner as in Example 1; 0.5 g; 5.88×10⁻⁵ mole) was added to the reaction system, stirring was further continued for additional one hour at a temperature of 21° to 30° C., then the stirring was stopped and the contents of the flask were withdrawn.

The weight of the contents was determined and found to be 18.55 g.

The results of analysis of this product was as follows:
Solid content (nonvolatile content): 48.5% by weight
NCO content: 9.64% by weight
Free p-IEBI: 0.61% by weight The yield of this reaction was not lower than 99.0%.

The resulting polyisocyanato-isocyanurate was converted into a methyl carbamate compound, the carbamate was analyzed by GPC and it was found that the amount of each oligomer contained therein was as follows:

n=1 (trimer): 65.4%
n=2 (pentamer): 23.4%
n=3 to 5: 10.6%

As seen from the results of the GPC analysis, polyisocyanato-isocyanurates containing not lower than 40% by weight of trimers (n=1) could be obtained without accompanying the formation of higher polymers (n=6 or higher).

The N,N',N''-tris[4-(α-isocyanatoethyl)phenyl]isocyanurate obtained in this Example was likewise subjected to thermal analysis and it was also confirmed that it exhibited very excellent heat resistance. Moreover, the glass transition point of the resin obtained by polymerization in which the compound was used as a hardening agent was increased and when the weatherability thereof was examined, it was found that it showed almost no yellowing, i.e., high resistance to yellowing. Thus, it is ensured that the foregoing reaction product is a compound having useful properties.

EXAMPLE 4

Preparation of a Mixture of m- and p-Isocyanatomethylphenyl isocyanurate

To a flask similar to that used in Example 1, there were added 9.25 g (0.053 mole) of a mixture of (3-isocyanatophenyl)methylisocyanate and (4-isocyanatophenyl)methylisocyanate (weight ratio=55:45; prepared by phosgenation of a mixture of 3-aminobenzylamine and 4-aminobenzylamine; hereunder referred to as "IMBI") and 8.55 g (0.074 mole) of butyl acetate as a solvent to dissolve the IMBI and the solution was cooled to 5° C. with stirring while the content of the flask was blanketed with nitrogen gas. The catalyst B (1.25 g; 4.67×10⁻⁵ mole; prepared in the same manner as in Example 1) was added to the solution with stirring and when the stirring (600 rpm) was continued, the temperature of the solution initially rose up to 23° C. due to the heat of reaction. Thereafter, the flask was externally cooled or warmed to control the temperature of the solution to 20° C.

Lap samples were collected at predetermined intervals and the amount of unreacted free IMBI in each sample was determined by gas chromatography. The amount thereof reached a predetermined level (not higher than 1% by weight) about 8 hours after the addition of the catalyst B. Thus, the terminator C (prepared in the same manner as in Example 1; 0.040 g; 4.71×10⁻⁵ mole) was added to the reaction system, stirring was further continued for additional one hour at a temperature of 20° C., then the stirring was stopped and the contents of the flask were withdrawn.

The weight of the contents was determined and found to be 17.72 g.

The results of analysis of this product were as follows:
Solid content (nonvolatile content): 48.0% by weight
NCO content: 10.42% by weight
Free IMBI: 0 36% by weight The yield of this reaction was not lower than 99.0%.

The resulting polyisocyanato-isocyanurate was converted to a methyl carbamate compound, the carbamate was analyzed by GPC and it was found that the amount of each oligomer was as follows:

n=1 (trimer): 58.3%
n=2 (pentamer): 25.5%
n=3 to 5: 15.7%

The product obtained in this Example was likewise subjected to thermal analysis and it was also confirmed that it exhibited very excellent heat resistance. Moreover, the glass transition point of the resin obtained by polymerization in which the compound was used as a hardening agent was increased and when the weatherability thereof was examined, it was found that it showed almost no yellowing, i.e., high resistance to yellowing. Thus, it is ensured that the foregoing reaction product is a compound having useful properties.

REFERENCE EXAMPLE 3

Preparation of acryl polyol resins 126 g of 2-hydroxyethyl methacrylate, 390 g of methyl methacrylate, 100 g of n-butyl methacrylate, 188 g of n-butyl acrylate, 188 of ethyl acrylate and 12 of azobisisobutyronitrile (AIBN) were mixed together and the mixture was dropwise added continuously to 1000 g of n-butyl acetate refluxed over 5 hours with stirring and then the polymerization was continued for additional 2 hours while the refluxing was continued to thus give an acryl polyol having the following physical characteristics:

| Physical Characteristics of the Resulting Resin | |
|---|---|
| Appearance | colorless and transparent |
| Nonvolatile content | 50.21% |
| Viscosity (Gardner/25° C.) | Z₃ |
| Hydroxyl value (KOH mg/varnish) | 30 |

REFERENCE EXAMPLE 4

Preparation of Base Enamel

Base enamel was prepared by compounding the acryl polyol solution prepared in Reference Example 3 as described below.

The acryl polyol prepared in Reference Example 3: 45 g

Pigment: Titanium oxide R930 (available from Ishihara Sangyo Co.): 45 g

Thinner (a mixed solution of xylene/toluene/butyl acetate/methyl ethyl ketone): 10 g The above components were blended in the proportion listed above and the pigment was kneaded into the blend with a three-roll mill to obtain an intended base enamel.

EXAMPLE 5 TO 7 AND COMPARATIVE EXAMPLES 1 TO 4

Compositions for forming urethane resins according to the present invention was prepared by compounding each of solutions of polyisocyanato-isocyanurates obtained in Examples 1, 2 and 3, the acryl polyol resin solution as shown in Reference Example 3 and the base enamel prepared in Reference Example 4 so that the molar amount of the isocyanato group was equal to that of the hydroxyl group and the content of pigments (PWC) was 40% by weight; adding a thinner comprising ethyl acetate/toluene/butyl acetate/xylene/cellosolve acetate (weight ratio=30/30/20/15/5) and then adjusting to 15 sec./25° C. with Ford-Cup #4.

The resulting composition was coated on the surface of steel plates and glass plates with an air spray gun (IWATANI-77 Model; nozzle diameter 2 mmφ) so that the thickness of the film determined after drying was 25μ, allowed to stand at room temperature (20° C./60% RH) for 7 days and was used in the following tests.

For comparison, the same tests were also carried out using conventional samples, i.e., an organic polyisocyanate derived from tolylene diisocyanate (OLESTER P75 available from MITSUI TOATSU CHEMICALS, INC.) and three kinds of aliphatic polyisocyanates: (1) OLESTER NP1000 (available from MITSUI TOATSU CHEMICALS, INC.); (2) CORONATE EH (an isocyanurate derivative of hexamethylene diisocyanate available from NIPPON POLYURETHANE CO., LTD.); and (3) IPDI T1890 (DAICEL . HUELS Co., Ltd.).

Coated film performance and physical properties of these samples are listed in the following Table 1.

The tests on the properties of the coated films were performed at 20° C./60% RH and they were evaluated according to ji JIS K-5400. In Table 1, 1) to g) are as follows:

1) Adhesion: determined according to JIS D-0202.
2) Erichsen extrusion: determined according to JIS Z-2247.
3) Magic staining properties: determined according to JAS 1373. More specifically, a test piece is horizontally placed, a line of 10 mm wide was drawn on the surface of the test piece with a quick-drying ink defined in JIS S-6037(1964), allowed to stand for 24 hours and then wiped off with a cloth containing an alcohol. The results are estimated according to the following three stage evaluation standard.
   ○: there remains no mark;
   Δ: there remains slight mark;
   ×: there remains clear mark.
4) Xylene rubbing (50 times): A test piece was fixed on a tester for fastness to rubbing of dyed materials and cotton cloth containing 2 ml of xylene was moved back and forth for 50 times under a load of 500 g. The result is estimated according to the following three stage evaluation:
   ○: no abnormality;
   Δ: there remains slight rubbing mark;
   ×: the surface of the substrate can be seen.
5) Resistance to acids and alkalis: determined according to JAS 1373. More specifically, a test piece is horizontally placed, a 10% aqueous sulfuric acid solution (or a 10% aqueous sodium hydroxide solution) is dropwise added to the surface of the test piece, the surface is covered with a watch glass for 24 hours and then allowed to stand for 24 hours. The result is estimated according to the following three stage evaluation:
   ○: no abnormality;
   Δ: there remains slight mark;
   ×: there remains clear mark.
6) WOM degree of yellowing: determined according to JIS K-7103.
7) Gloss (60° gloss): determined according to JIS K-5400.
8) Du-Pont impact (½in/500 g): determined according to JIS K-5400.
9) Secondary Physical properties: After a sample is immersed in boiling water for 4 hours, physical properties are determined.

EXAMPLE 8 AND COMPARATIVE EXAMPLES 5 TO 8

The same tests as those in Example 5 were performed on a typical commercially available acryl polyol resin, i.e., OLESTER Q 182 (MITSUI TOATSU CHEMICALS. INC.; number average molecular weight=9,500; content of solids=50%; hydroxyl value=45 KOHmg/g) and a base enamel prepared on the basis of the OLESTER Q 182. The same procedures used in Example 5 were repeated except that a different compound having active hydrogen atoms was employed.

On the other hand, the same tests were performed on the four kinds of the aliphatic polyisocyanates used in Comparative Examples 1 to 4. The results obtained are summarized in the following Table 2.

Tests on quality of coated films and methods for evaluation were the same as those employed in Example 5.

EXAMPLE 9 AND COMPARATIVE EXAMPLES 9 TO 12

The same tests as those in Example 5 were performed on a commercially available polyester polyol resin, i.e., OLESTER Q 173 (MITSUI TOATSU CHEMICALS, INC.; content of solids=100%; hydroxyl value=256 KOHmg/g) and base enamel prepared on the basis of the OLESTER Q 173. The same procedures used in Example 5 were repeated except that a different compound having active hydrogen atoms was employed.

On the other hand, the same tests were performed on the four kinds of the aliphatic polyisocyanates used in Comparative Examples 1 to 4. The results obtained are summarized in the following Table 3.

Tests on quality of coated films and methods for evaluation were the same as those employed in Example 5.

EXAMPLE 10

The same tests used in Example 6 were performed on a sample which had the same composition as that used in Example 6 except that an organic polyisocyanate component used was a solution of the isocyanurate type polyisocyanate solution obtained in Example 1 to which commercially available OLESTER NP 1000 (1/1 weight ratio) was added. The results obtained are listed in the following Table 2.

Tests on quality of coated films and methods for evaluation were the same as those employed in Example 6.

EXAMPLE 11

The same tests used in Example 6 were performed on a sample which had the same composition as that used in Example 6 except that an organic polyisocyanate component used was a solution of the polyisocyanato-isocyanurate solution obtained in Example 1 to which commercially available OLESTER NP 1000 (1/5 weight ratio) was added. The results obtained ar listed in the following Table 2.

Tests on quality of coated films and methods for evaluation were the same as those employed in Example 5.

TABLE 1

| | Example 5 | Example 6 | Example 7 | Comp. Ex. 1 | Comp. Ex. 2 | Comp. Ex. 3 | Comp. Ex. 4 |
|---|---|---|---|---|---|---|---|
| Compunding | | | | | | | |
| Isocyanate | Example 1 | Example 2 | Example 3 | OLESTER NP1000 | CORONATE EH | IPDI T = 1890 | OLESTER P75 |
| Active H-containing compound | Acryl polyol of Reference Example 3 and base enamel of reference Example 4 | | | | | | |
| Compatibility | good | good | good | good | good | good | good |
| Reactivity | | | | | | | |
| Set to touch (min.) | 10 | 10 | 10 | 13 | 13 | 15 | 8 |
| Complete hardening (min.) | 225 | 225 | 225 | 300 | 300 | 270 | 100 |
| Pot life (hr.) | ≧24 | ≧24 | ≧24 | ≧24 | ≧24 | ≧24 | 20 |
| Film appearance | good | good | good | good | good | good | good |
| Film thickness ($\mu$) | 22.7 | 22.3 | 23.1 | 24.3 | 23.8 | 24.1 | 25.4 |
| Gloss (60° gloss) 7) | 92 | 92 | 92 | 92 | 89 | 88 | 85 |
| Erichsen extrusion (cm) 2) | ≧8 | ≧8 | ≧8 | ≧8 | ≧8 | ≧8 | 3.27 |
| DuPont impact (½ in/500 g) 8) | ≧50 | ≧50 | ≧50 | ≧50 | ≧50 | ≧50 | 25 |
| Magic ink staining 3) | | | | | | | |
| (Red) | ○ | ○ | ○ | △ | ○ | ○ | ○ |
| (Black) | ○ | ○ | ○ | △ | △ | △ | ○ |
| (Blue) | ○ | ○ | ○ | △ | ○ | X | ○ |
| Xylene rubbing (50 times) 4) | ○ | ○ | ○ | △ | △ | △ | ○ |
| Adhesion 1) | 100/100 | 100/100 | 100/100 | 100/100 | 100/100 | 100/100 | 50/100 |
| Pencil hardness | H | H | H | F | H | H | H |
| Resistance to acid 5) | ○ | ○ | ○ | ○ | ○ | ○ | ○ |
| Resistance to alkali 5) | ○ | ○ | ○ | ○ | ○ | ○ | ○ |
| Secondary physical properties | | | | | | | |
| Appearance | no change | no change | no change | no change | no change | no change | no change |
| Gloss (60° gloss) 7) | 90 | 90 | 90 | 89 | 88 | 85 | 82 |
| Erichsen extrusion (cm) 2) | 5.23 | 5.51 | 5.18 | 5.41 | 5.02 | 3.56 | 0.28 |
| DuPont impact (½ in/500 g) 8) | 45 | 45 | 45 | 45 | 40 | 20 | 10 |
| Adhesion 1) | 100/100 | 100/100 | 100/100 | 100/100 | 100/100 | 100/100 | 0/100 |
| WOM degree of yellowing ($\Delta E$) 6) | | | | | | | |
| 200 hrs. | 0.48 | 0.49 | 0.42 | 0.45 | 0.42 | 0.52 | 3.62 |
| 500 hrs. | 0.84 | 0.91 | 0.82 | 0.85 | 0.73 | 0.91 | 4.53 |
| 1000 hrs. | 2.10 | 2.23 | 2.04 | 2.13 | 1.69 | 2.02 | 5.68 |

TABLE 2

| | Example 8 | Comp. Ex. 5 | Comp. Ex. 6 | Comp. Ex. 7 | Comp. Ex. 8 | Example 10 | Example 11 |
|---|---|---|---|---|---|---|---|
| Compunding | | | | | | | |
| Isocyanate | Example 1 | OLESTER NP1000 | CORONATE EH | IPDI T = 1890 | OLESTER P75 | Ex. 12/ OLESTER NP1000 = 1/1 | Ex. 12/ OLESTER NP1000 = 1/5 |
| Content of IEBI isocyanurate type polyisocyanate in the total amount of organic polyisocyanate (wt %) | 100 | 0 | 0 | 0 | 0 | 40 | 12 |
| Active H-containing compound | | | | OLESTER Q182 | | | |
| Compatibility | good | good | good | good | good | good | good |
| Reactivity | | | | | | | |
| Set to touch (min.) | 8 | 9 | 9 | 10 | 7 | 9 | 9 |
| Complete hardening (min.) | 195 | 260 | 260 | 230 | 90 | 200 | 230 |
| Pot life (hr.) | ≧24 | ≧24 | ≧24 | ≧24 | 10 | ≧24 | ≧24 |
| Film appearance | good | good | good | good | good | good | good |
| Film thickness ($\mu$) | 22.0 | 21.7 | 23.0 | 22.5 | 23.5 | 23.0 | 22.7 |
| Gloss (60° gloss) 7) | 90.3 | 88.2 | 84.4 | 85.0 | 83.2 | 86.2 | 87.1 |
| Erichsen extrusion (cm) 2) | 2.51 | 7.45 | 7.67 | 0.10 | 0.12 | 4.27 | 6.23 |
| DuPont impact (½ in/500 g) 8) | 20 | 30 | 15 | 15 | 10 | 20 | 30 |
| Magic ink staining 3) | | | | | | | |
| (Red) | ○ | △ | ○ | X | ○ | ○ | △ |
| (Black) | ○ | X | △ | X | ○ | △ | X |
| (Blue) | ○ | X | △ | X | ○ | ○ | △ |
| Xylene rubbing (50 times) 4) | ○ | △ | △ | X | ○ | ○ | △ |
| Adhesion 1) | 100/100 | 100/100 | 100/100 | 100/100 | 100/100 | 100/100 | 100/100 |
| Pencil hardness | 2H | H | 2H | H | 2H | 2H | H |
| Resistance to acid 5) | ○ | ○ | ○ | ○ | ○ | ○ | ○ |

TABLE 2-continued

|  | Example 8 | Comp. Ex. 5 | Comp. Ex. 6 | Comp. Ex. 7 | Comp. Ex. 8 | Example 10 | Example 11 |
|---|---|---|---|---|---|---|---|
| Resistance to alkali 5) | ○ | ○ | ○ | ○ | ○ | ○ | ○ |
| Secondary physical properties | | | | | | | |
| Appearance | no change | no change | no change | no change | no change | no change | no change |
| Gloss (60° gloss) 7) | 88.5 | 84.0 | 84.4 | 84.5 | 82.2 | 84.2 | 84.3 |
| Erichsen extrusion (cm) 2) | 0.51 | 5.34 | 6.42 | 0.12 | 0.20 | 2.35 | 4.29 |
| DuPont impact (½ in/500 g) 8) | 20 | 25 | 25 | 20 | 10 | 20 | 25 |
| Adhesion 1) | 100/100 | 100/100 | 100/100 | 70/100 | 0/100 | 100/100 | 100/100 |
| WOM degree of yellowing (ΔE) 6) | | | | | | | |
| 200 hrs. | 0.44 | 0.35 | 0.42 | 0.53 | 3.82 | 0.65 | 0.47 |
| 500 hrs. | 0.77 | 0.78 | 0.65 | 0.82 | 4.57 | 1.24 | 0.85 |
| 1000 hrs. | 2.18 | 2.15 | 1.88 | 2.25 | 5.29 | 2.58 | 2.08 |

TABLE 3

|  | Example 9 | Comp. Ex. 9 | Comp. Ex. 10 | Comp. Ex. 11 | Comp. Ex. 12. |
|---|---|---|---|---|---|
| Compunding | | | | | |
| Isocyanate | Example 1 | OLESTER NP1000 | CORONATE EH OLESSTER Q173 | IPDI T = 1890 | OLESTER P75 |
| Active H-containing compound | | | | | |
| Compatibility | good | good | good | good | good |
| Reactivity | | | | | |
| Set to touch (min.) | 60 | 69 | 69 | 78 | 55 |
| Complete hardening (hr.) | 20 | 24 | 24 | 25 | 9.5 |
| Pot life (hr.) | ≧48 | ≧48 | ≧48 | ≧48 | 22 |
| Film appearance | good | good | good | good | good |
| Film thickness (μ) | 25.9 | 26.7 | 25.2 | 24.9 | 25.7 |
| Gloss (60° gloss) 7) | 98.3 | 98.9 | 98.0 | 98.5 | 98.3 |
| Erichsen extrusion (cm) 2) | ≧8 | ≧8 | ≧8 | ≧8 | ≧8 |
| DuPont impact (½ in/500 g) 8) | ≧50 | ≧50 | ≧50 | ≧50 | ≧50 |
| Magic ink staining 3) | | | | | |
| (Red) | Δ | X | X | X | ○ |
| (Black) | Δ | X | X | X | ○ |
| (Blue) | ○ | X | Δ | X | ○ |
| Xylene rubbing (50 times) 4) | Δ | X | Δ | X | ○ |
| Adhesion 1) | 100/100 | 100/100 | 100/100 | 100/100 | 0/100 |
| Pencil hardness | F | B | F | B | H |
| Resistance to acid 5) | ○ | ○ | ○ | ○ | ○ |
| Resistance to alkali 5) | ○ | ○ | ○ | ○ | ○ |
| Secondary physical properties | | | | | |
| Appearance | no change | no change | no change | no change | no change |
| Gloss (60° gloss) 7) | 97.5 | 97.3 | 96.2 | 96.2 | 97.1 |
| Erichsen extrusion (cm) 2) | ≧8 | ≧8 | ≧8 | ≧8 | 3.91 |
| DuPont impact (½ in/500 g) 8) | ≧50 | ≧50 | ≧50 | ≧50 | 20 |
| Adhesion 1) | 100/100 | 100/100 | 100/100 | 100/100 | 0/100 |
| WOM degree of yellowing (ΔE) 6) | | | | | |
| 200 hrs. | 0.61 | 0.59 | 0.50 | 0.62 | 4.93 |
| 500 hrs. | 1.25 | 1.23 | 1.10 | 1.33 | 6.58 |
| 1000 hrs. | 2.49 | 2.57 | 2.03 | 2.77 | 7.81 |

What is claimed is:

1. A polyisocyanato-isocyanurate represented by the following general formula (I):

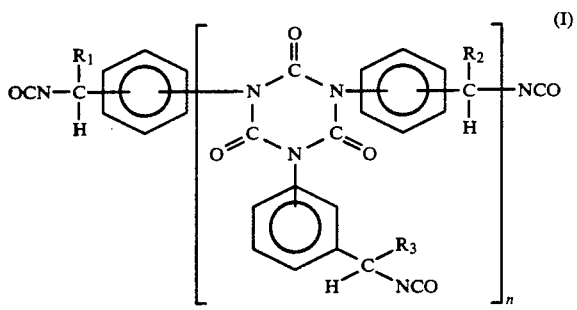

wherein n is an integer ranging from 1 to 5 and $R_1$, $R_2$ and $R_3$ may be same or different and each represent hydrogen atom or a lower alkyl group.

2. Polyisocyanato-isocyanurates represented by the foregoing general formula (I) of claim 1 in which n is 1 and $R_1$, $R_2$ and $R_3$ are hydrogen atom or a lower alkyl group having 1 to 5 carbon atoms.

3. Polyisocyanato-isocyanurates represented by the foregoing general formula (I) of claim 1 in which n is an integer ranging from 2 to 5 and $R_1$, $R_2$ and $R_3$ are hydrogen atom or a lower alkyl group having 1 to 5 carbon atoms.

4. Polyisocyanato-isocyanurate of claim 1 wherein it comprises 40 to 90% by weight of the polyisocyanato isocyanurate represented by the foregoing general formula (I) in which n is 1 and the balance of the polyisocyanato-isocyanurate of the formula (I) in which n is an integer range from 2 to 5.

5. A method for preparing polyisocyanato-isocyanurate represented by the foregoing general formula (I) comprising polymerizing an α-(isocyanatophenyl)alkylisocyanate represented by the following general formula (II):

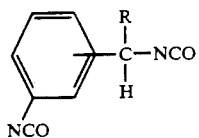

wherein R represents hydrogen atom or a lower alkyl group having 1 to 5 carbon atoms, provided that the isocyanato group bonded to the phenyl group may be in either of the m- and p-positions in the presence of a trimerization catalyst.

6. The method for preparing polyisocyanato-isocyanurate of claim 5 wherein the polymerization is continued until an amount of the remaining diisocyanate monomer become not more than 1% by weight on the basis of a solid of the polymerized product.

7. The method for preparing polyisocyanato-isocyanurate of claim 5 wherein the trimerization catalyst comprises a tertiary amine or a quaternary ammonium compound and optionally an epoxide compound.

8. The method for preparing polyisocyanato-isocyanurate of claim 7 wherein the polymerization is continued until an amount of the remaining diisocyanate monomer become not more than 1% by weight on the basis of a solid of the polymerized product.

9. An organic polyisocyanate comprising a polyisocyanato isocyanurate represented by the foregoing general formula (I) in an amount of not lower than 10% by weight.

* * * * *